US012564330B2

(12) United States Patent
Ha

(10) Patent No.: US 12,564,330 B2
(45) Date of Patent: Mar. 3, 2026

(54) MACHINE LEARNING METHOD FOR PREDICTING FRACTIONAL FLOW RESERVE FOR OPTICAL COHERENCE TOMOGRAPHY

(71) Applicant: RAYWATT INC., Seoul (KR)

(72) Inventor: Jin Yong Ha, Seoul (KR)

(73) Assignee: RAYWATT INC., Seoul (KR)

( * ) Notice: Subject to any disclaimer, the term of this patent is extended or adjusted under 35 U.S.C. 154(b) by 0 days.

(21) Appl. No.: 18/678,615

(22) Filed: May 30, 2024

(65) Prior Publication Data

US 2024/0306926 A1 Sep. 19, 2024

Related U.S. Application Data

(63) Continuation of application No. PCT/KR2022/017372, filed on Nov. 7, 2022.

(30) Foreign Application Priority Data

Dec. 21, 2021 (KR) ........................ 10-2021-0183326

(51) Int. Cl.
| | |
|---|---|
| *A61B 5/026* | (2006.01) |
| *A61B 5/00* | (2006.01) |
| *A61B 5/02* | (2006.01) |

(52) U.S. Cl.
CPC .......... *A61B 5/0261* (2013.01); *A61B 5/0044* (2013.01); *A61B 5/02007* (2013.01);
(Continued)

(58) Field of Classification Search
CPC . A61B 5/0261; A61B 5/0044; A61B 5/02007; A61B 5/7267; A61B 5/7275;
(Continued)

(56) References Cited

U.S. PATENT DOCUMENTS

2019/0200880 A1* 7/2019 Sharma ................ A61B 5/7264

FOREIGN PATENT DOCUMENTS

| KR | 10-2017-0090284 A | 8/2017 |
|---|---|---|
| KR | 10-2017-0113515 A | 10/2017 |

(Continued)

OTHER PUBLICATIONS

International Search Report issued from PCT International Application No. PCT/KR2022/017372 issued on Mar. 23, 2023.
(Continued)

*Primary Examiner* — Serkan Akar
(74) *Attorney, Agent, or Firm* — James Y Kim

(57) ABSTRACT

A method for predicting fractional flow reserve on the basis of machine learning is disclosed. The disclosed method for predicting fractional flow reserve comprises the steps of: receiving a class of a target cardiac blood vessel and a feature value for the target cardiac blood vessel extracted from an optical coherence tomography (OCT) image of a lumen of the target cardiac blood vessel; and predicting an FFR value for the target cardiac blood vessel using at least one pretrained predictive model, the class of the target cardiac blood vessel, and the feature value, wherein the feature value includes at least one of a proximal lumen area (PLA) value, a minimal lumen area (MLA) value, a percent area stenosis value, a distal lumen area (DLA) value, a lesion length value, a rupture presence/absence value, a plaque area value, and a lipid rich value.

6 Claims, 3 Drawing Sheets

(52) U.S. Cl.
CPC .......... *A61B 5/7267* (2013.01); *A61B 5/7275*
(2013.01); *A61B 2576/023* (2013.01)

(58) Field of Classification Search
CPC .......... A61B 2576/023; A61B 5/02028; A61B
5/1075; A61B 5/1076; A61B 5/1079;
A61B 5/0066; A61B 5/0033; A61B
5/7264; G06N 20/00; G16H 30/40; G16H
50/20; G16H 50/50
See application file for complete search history.

(56) References Cited

FOREIGN PATENT DOCUMENTS

| | | | |
|---|---|---|---|
| KR | 10-2021-0016862 | A | 2/2021 |
| KR | 10-2021-0092963 | A | 7/2021 |
| KR | 10-2190431 | B1 | 12/2022 |

OTHER PUBLICATIONS

Written Opinion of International Search Authority for PCT International Application No. PCT/KR2022/017372 issued on Mar. 23, 2023.

* cited by examiner

MACHINE LEARNING METHOD FOR PREDICTING FRACTIONAL FLOW RESERVE FOR OPTICAL COHERENCE TOMOGRAPHY

CROSS-REFERENCE TO RELATED APPLICATION

This application is a bypass continuation of PCT International Application No. PCT/KR2022/017372, which was filed on Nov. 7, 2022, and which claims priority to and the benefit of Korean Patent Application No. 2021-00183326, filed on Dec. 21, 2021, the disclosures of which are incorporated herein by reference in its entirety.

TECHNICAL FIELD

The present disclosure relates to a method of predicting a fractional flow reserve (FFR) on the basis of machine learning, and more particularly, to a training method for predicting an FFR of a coronary artery disease patient and a method of predicting an FFR of a coronary artery disease patient using a predictive model acquired through such training.

BACKGROUND ART

A fractional flow reserve (FFR) is the ratio of the maximum blood flow in a distal blood vessel of a coronary stenosis to the maximum blood flow in a normal proximal blood vessel. Here, the proximal blood vessel is a blood vessel close to the heart in the coronary arteries while the distal blood vessel is a blood vessel farther away from the heart.

An FFR value of 0.75 at a site of a coronary stenosis represents that coronary blood flow is reduced by up to 25% compared to normal coronary vessels.

Since an FFR value decreases at a site of a coronary stenosis in this way, an FFR value may be used to determine whether coronary arteries, that is, cardiovascular vessels, are stenotic or not, and to decide on a stent insertion procedure.

Such an FFR value may be calculated as a ratio of pressure at a distal part of a lesion to pressure at a proximal part of the lesion which is measured using a pressure wire after induction of maximal hyperemia by intracoronary bolus injection or continuous intravenous infusion of adenosine.

Alternatively, according to a non-invasive method, lumens may be extracted from a cross-sectional image of a blood vessel, and then an FFR value may be measured by flow analysis based on a three-dimensional (3D) cardiovascular model. Such an image-based FFR measurement method is not easily applicable to medical sites due to considerable modeling and simulation time.

DISCLOSURE

Technical Problem

The present disclosure is directed to providing a method of rapidly and accurately predicting a fractional flow reserve (FFR) that can be used in medical sites.

The present disclosure is also directed to providing a method of predicting an FFR that can provide information required for a patient's stent insertion procedure.

Technical Solution

One aspect of the present disclosure provides a method of predicting a fractional flow reserve (FFR) on the basis of machine learning, the method including: receiving a class of a target cardiac blood vessel and a feature value for the target cardiac blood vessel extracted from an optical coherence tomography (OCT) image of a lumen of the target cardiac blood vessel; and predicting an FFR value for the target cardiac blood vessel using at least one pretrained predictive model, the class of the target cardiac blood vessel, and the feature value. The feature value includes at least one of a proximal lumen area (PLA) value, a minimal lumen area (MLA) value, a percent area stenosis value, a distal lumen area (DLA) value, a lesion length value, a rupture presence/absence value, a plaque area value, and a lipid rich value.

Another aspect of the present disclosure provides a method of predicting an FFR on the basis of machine learning, the method including: generating a feature value for a target cardiac blood vessel from an OCT image of a lumen of the target cardiac blood vessel; and predicting an FFR value for the target cardiac blood vessel using at least one pretrained predictive model, a class of the target cardiac blood vessel, and the feature value. The feature value includes at least one of a PLA value, an MLA value, a percent area stenosis value, a DLA value, a lesion length value, a rupture presence/absence value, a plaque area value, and a lipid rich value.

Advantageous Effects

According to an embodiment of the present disclosure, it is possible to provide an accurate fractional flow reserve (FFR) prediction result using a feature value acquired from an optical coherence tomography (OCT) image.

According to an embodiment of the present disclosure, it is also possible to provide an accurate prediction result by predicting an FFR in consideration of a class of a cardiac blood vessel from which a feature value is acquired.

MODES OF THE INVENTION

Figure 1:
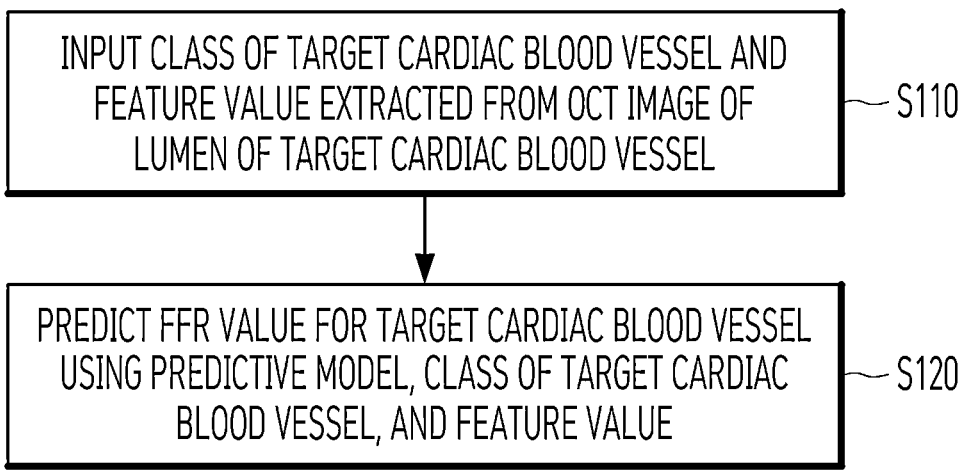
FIG. 1 is a flowchart illustrating a method of predicting a fractional flow reserve (FFR) on the basis of machine learning according to an embodiment of the present disclosure.

Since the present disclosure can be variously modified and have several embodiments, specific embodiments will be illustrated in the drawings and described in detail in the detailed description. However, this is not intended to limit the present disclosure to the specific embodiments, and it is to be understood that the present disclosure includes all modifications, equivalents, and substitutions within the spirit and technical scope of the present disclosure. In describing each drawing, like reference numerals are used for like components.

The present disclosure relates to a method of predicting a coronary artery disease patient's fractional flow reserve (FFR) using a feature value extracted from an optical coherence tomography (OCT) image. According to the present disclosure, it is possible to rapidly and accurately predict an FFR through machine learning, and thus the present disclosure is applicable to medical sites.

According to an embodiment of the present disclosure, an FFR is predicted using a feature value extracted from an OCT image. OCT is a technology for imaging a microstructure of biological tissues by combining the interference of light with the principles of confocal microscopy and shows higher resolution than ultrasound, computed tomography (CT), and magnetic resonance imaging (MRI). Therefore, according to an embodiment of the present disclosure in which an FFR is predicted using a feature value extracted from an OCT image, it is possible to acquire an accurate FFR prediction result.

A method of predicting an FFR according to an embodiment of the present disclosure may be performed in a computing device including a processor.

Hereinafter, embodiments of the present disclosure will be described in detail with reference to the accompanying drawings.

FIG. 1 is a flowchart illustrating a method of predicting an FFR on the basis of machine learning according to an embodiment of the present disclosure.

Referring to FIG. 1, a computing device according to an embodiment of the present disclosure receives a class of a target cardiac blood vessel and a feature value for the target cardiac blood vessel (S110). The feature value is extracted from an OCT image of the lumen of the target cardiac blood vessel and may include at least one of a proximal lumen area (PLA) value, a minimal lumen area (MLA) value, a percent area stenosis value, a distal lumen area (DLA) value, a lesion length value, a rupture presence/absence value, a plaque area value, and a lipid rich value.

The MLA represents the area of the blood vessel at a point where the width of the vessel lumen, that is, the width between vessel wall surfaces, is the smallest at the site of a stenotic lesion, and the PLA represents the area of the blood vessel at a point where the width of the lumen is the largest in the lumen toward the heart from the point where the width of the lumen is the smallest. The DLA represents the area of the blood vessel at a point where the width of the lumen is the largest in the lumen away from the heart from the point where the width of the lumen is the smallest. The lesion length value represents the length of the blood vessel from the point of the PLA to the point of the DLA, and the percent area stenosis represents the degree of narrowing of the blood vessel at the lesion site. The rupture presence/absence value represents whether there is a rupture in the lesion site, and the plaque area value represents the area of plaque at the lesion site. Finally, the lipid rich value represents the amount of lipid in the lesion site.

The feature value may be generated by a separate computing device for extracting a feature value or determined by a medical specialist analyzing the OCT image. According to some embodiments, a computing device according to an embodiment of the present disclosure may generate the feature value from the OCT image of the lumen of the target cardiac blood vessel.

The computing device according to the embodiment of the present disclosure predicts an FFR value for the target cardiac blood vessel using at least one pretrained predictive model, the class of the target cardiac blood vessel, and the feature value of the target cardiac blood vessel (S120). Depending on the physical condition or state of the patient, a target cardiac blood vessel from which an OCT image may be acquired may vary among various types of cardiac blood vessels. Accordingly, the computing device predicts the FFR value using the class of the target cardiac blood vessel from which the OCT image is acquired.

According to some embodiments, the computing device may predict the FFR value to be one value between 0 and 1 or may output 0 when the predicted FFR value is a preset threshold value, for example, 0.6, or larger, or output 1 when the predicted FFR value is smaller than the threshold value.

The FFR value predictive model may be based on various learning algorithms and may be a predictive model based on a random forest algorithm or an artificial neural network.

Figure 2:
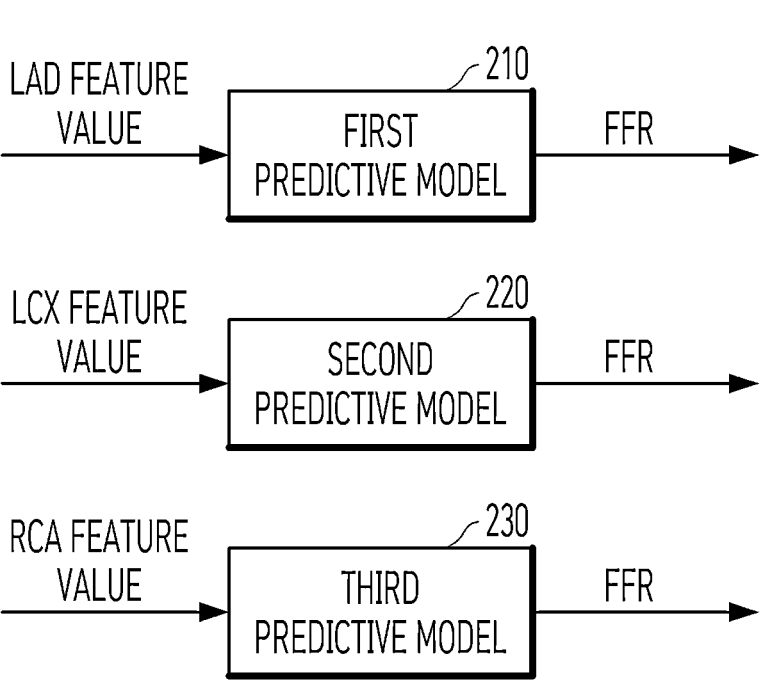
FIG. 2 is a set of diagrams of predictive models according to an embodiment of the present disclosure.

FIG. 2 is a set of diagrams of predictive models according to an embodiment of the present disclosure.

In operation S120, the computing device according to the embodiment of the present disclosure may select a predictive model corresponding to the class of a target cardiac blood vessel from among predictive models for predicting FFR values for cardiac blood vessels of different classes and predict an FFR value using the selected predictive model. Here, the class of a cardiac blood vessel may be left anterior descending artery (LAD), left circumflex artery (LCX), or right coronary artery (RCA).

Referring to FIG. 2, predictive models are models that are trained using training feature values for cardiac blood vessels of different classes. A first predictive model 210 is trained using training feature values acquired from LADs and FFR values for the LADs and predicts the FFR value for an LAD. A second predictive model 220 is trained using training feature values acquired from LCXs and FFR values for the LCXs and predicts the FFR value for an LCX. A third predictive model 230 is trained using training feature values acquired from RCAs and FFR values for the RCAs and predicts the FFR value for an RCA.

The predictive models are trained using different training feature value groups. The first predictive model 210 is trained using a training feature value group including percent area stenosis values, MLA values, lesion length values, and rupture presence/absence values acquired from the OCT images of LADs, and the second predictive model 220 is trained using a training feature value group including percent area stenosis values, MLA values, DLA values, lesion length values, and plaque area values acquired from the OCT images of LCXs. The third predictive model 230 is trained using a training feature value group including MLA values, percent area stenosis values, DLA values, plaque area values, and lipid rich values acquired from the OCT images of RCAs.

The computing device selects the first predictive model to predict an FFR value when the class of the target cardiac blood vessel is LAD, and selects the second predictive model 220 to predict an FFR value when the class of the target cardiac blood vessel is LCX. When the class of the target cardiac blood vessel is RCA, the computing device selects the third predictive model 230 to predict an FFR value.

The computing device predicts an FFR value using a feature value group corresponding to training feature values of each predictive model. In other words, the computing device predicts an FFR value using a different feature value group depending on the class of the target cardiac blood vessel. The computing device inputs a feature value group including percent area stenosis values, MLA values, lesion length values, and rupture presence/absence values acquired from the OCT images of LADs to the first predictive model 210 when the class of the target cardiac blood vessel is LAD, and inputs percent area stenosis values, MLA values, DLA values, lesion length values, and plaque area values to the second predictive model 220 when the class of the target cardiac blood vessel is LCX. When the class of the target cardiac blood vessel is RCA, the computing device inputs a feature value group including MLA values, percent area stenosis values, DLA values, plaque area values, and lipid rich values acquired from the OCT images of RCAs to the third predictive model 230.

Meanwhile, when the FFR value is within a set threshold range, the computing device according to the embodiment of the present disclosure may add the feature value to the feature value group to predict an FFR value, and the threshold range may be determined according to the class of the target cardiac blood vessel.

In general, a stenosis causing myocardial ischemia is known to be present when the FFR value of a lesion site is smaller than 0.75, and a stenosis is known not to cause myocardial ischemia when the FFR value of a lesion site is larger than 0.8. When the FFR value of a lesion site is between 0.75 and 0.8, it is unclear that whether a stenosis causes myocardial ischemia. Accordingly, when a previously predicted FFR value is within the preset threshold range, the computing device may input additional feature values in addition to existing feature values included in the feature value group to the predictive model and may predict a more accurate FFR value. The computing device may additionally input one of the foregoing feature values to the predictive model, and the additionally input feature value may be preset.

Since the predictive models may differ in accuracy, the computing device may additionally use feature values according to a threshold range which is adjusted on the basis of the class of the target cardiac blood vessel. The width of the threshold range may be set in inverse proportion to the accuracy of the predictive model. For example, when the second predictive model 220 has the highest accuracy, the width of the threshold range may be set to be the smallest, and when the third predictive model 230 has the lowest accuracy, the width of the threshold range may be set to be the largest.

With an increase in the number of generated feature values, a time and cost required for generating a feature value increase. Therefore, according to an embodiment of the present disclosure, when the uncertainty of a prediction result is high, an FFR value is predicted using additional feature values.

Figure 3:
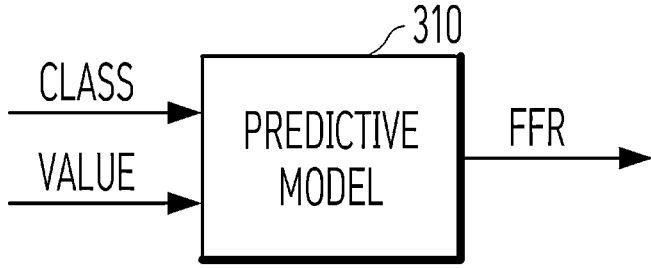
FIG. 3 is a diagram of a predictive model according to another embodiment of the present disclosure.

FIG. 3 is a diagram of a predictive model according to another embodiment of the present disclosure.

In operation S120, the computing device may predict an FFR value by inputting the class and feature value of the target cardiac blood vessel to the predictive model. Here, the feature value may include a percent area stenosis value, an MLA value, and a DLA value.

Unlike the predictive models of FIG. 2, a predictive model 310 of FIG. 3 is not separated by each class of a cardiac blood vessel and predicts an FFR value regardless of the class of a cardiac blood vessel. Training data used for training the predictive model of FIG. 3 includes not only training feature values and FFR values for the training feature values but also the classes of cardiac blood vessels from which the training feature values are acquired.

Accordingly, the computing device predicts an FFR value by inputting not only a feature value of a target cardiac blood vessel but also the class of the target cardiac blood vessel to the predictive model 310. All feature values input to the predictive model may be the same for each class of a target cardiac blood vessel.

The above-described technical details may be implemented in the form of program instructions that can be executed by various computing devices and recorded on a computer-readable medium. The computer-readable medium may include program instructions, data files, data structures, and the like solely or in combination. The program instructions recorded on the medium may be specially designed and constructed for embodiments or may be known and available to those of ordinary skill in the art of computer software. Examples of the computer-readable recording medium include magnetic media, such as a hard disk, a floppy disk, and magnetic tape, optical media, such as a compact disc (CD)-read only memory (ROM) and a digital versatile disc (DVD), magneto-optical media, such as a floptical disk, and hardware devices specially constructed to store and execute program instructions such as a ROM, a random-access memory (RAM), a flash memory, and the like. Examples of the program instructions include not only a machine language code generated by a compiler but also a high-level language code which is executable by a computer using an interpreter or the like. A hardware device may be configured to operate as one or more software modules to perform operations of embodiments, and vice versa.

Although the present disclosure has been described with reference to particular matters, such as detailed components, limited embodiments, and drawings, these are merely provided to help overall understanding of the present disclosure, and the present disclosure is not limited to the embodiments. Those of ordinary skill in the art can make various alterations and modifications from the embodiments. Therefore, the spirit of the present disclosure should not be limited to the described embodiments, and it should be construed that the following claims and all equivalents or equivalent modifications of the claims fall within the scope of the present disclosure.

What is claimed is:

1. A method of predicting a fractional flow reserve (FFR) on the basis of machine learning, the method performed by a computing device including a processor comprising:

receiving, by the computing device, data from an optical coherence tomography (OCT) imaging device, the data including a class of a target cardiac blood vessel and a feature value for the target cardiac blood vessel extracted through an analysis, by the processor, of an optical coherence tomography (OCT) image of a lumen of the target cardiac blood vessel; and processing the data, by the processor, to predict an FFR value for the target cardiac blood vessel using at least one pretrained predictive model, wherein the predicting of the FFR value further comprises:

using a different feature value group depending on the class of the target cardiac blood vessel, inputting the class of the target cardiac blood vessel and a feature value group corresponding the class of the target cardiac blood vessel to the pretrained predictive model to generate the FFR value, and selecting a predictive model corresponding to the class of the target cardiac blood vessel from among predictive models for predicting FFR values for cardiac blood vessels of different classes; and predicting the FFR value using the selected predictive model, wherein determining that the FFR value is within a preset threshold range, providing additional feature values to the feature value group and predicting the FFR value, wherein the preset threshold range is determined according to the class of the target cardiac blood vessel and the preset threshold range is a range in which it is uncertain whether a stenosis is causing myocardial ischemia, and

wherein the feature value group includes feature values selected from a group consisting of a proximal lumen area (PLA) value, a minimal lumen area (MLA) value, a percent area stenosis value, a distal lumen area (DLA) value, a lesion length value, a rupture presence/absence value, a plaque area value, and a lipid rich value.

2. The method of claim 1, wherein the predicting of the FFR value comprises:

selecting a predictive model corresponding to the class of the target cardiac blood vessel from among predictive models for predicting FFR values for cardiac blood vessels of different classes; and predicting the FFR value using the selected predictive model.

3. The method of claim 2, wherein the class of the target cardiac blood vessel includes left anterior descending artery (LAD), left circumflex artery (LCX), or right coronary artery (RCA).

4. The method of claim 3, wherein the predicting of the FFR value comprises, upon determining the class of the target cardiac blood vessel is the left anterior descending artery (LAD), predicting the FFR value using a feature value group including a group consisting of the percent area stenosis value, the MLA value, the lesion length value, and the rupture presence/absence value.

5. The method of claim 3, wherein the predicting of the FFR value comprises, upon determining the class of the target cardiac blood vessel is the left circumflex artery (LCX), predicting the FFR value using a feature value group including at least one feature value selected from a group consisting of the percent area stenosis value, the MLA value, the PLA value, the lesion length value, and the plaque area value.

6. The method of claim 3, wherein the predicting of the FFR value comprises, upon determining the class of the target cardiac blood vessel is the right coronary artery (RCA), predicting the FFR value using a feature value group including at least one feature value selected from a group consisting of the MLA value, the percent area stenosis value, the DLA value, the plaque area value, and the lipid rich value.

* * * * *